United States Patent
Maeda et al.

(10) Patent No.: US 9,970,951 B2
(45) Date of Patent: May 15, 2018

(54) GENETIC TESTING DEVICE, GENETIC TESTING METHOD AND PROGRAM

(71) Applicant: HITACHI HIGH-TECHNOLOGIES CORPORATION, Tokyo (JP)

(72) Inventors: Koshi Maeda, Tokyo (JP); Hiroko Fujita, Tokyo (JP); Yoshiyuki Shoji, Tokyo (JP); Ryoji Inaba, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 168 days.

(21) Appl. No.: 14/652,537

(22) PCT Filed: Dec. 19, 2013

(86) PCT No.: PCT/JP2013/084040
§ 371 (c)(1),
(2) Date: Jun. 16, 2015

(87) PCT Pub. No.: WO2014/103858
PCT Pub. Date: Jul. 3, 2014

(65) Prior Publication Data
US 2015/0346228 A1  Dec. 3, 2015

(30) Foreign Application Priority Data
Dec. 28, 2012 (JP) .................. 2012-286469

(51) Int. Cl.
*G01N 35/00* (2006.01)
*G01N 35/02* (2006.01)
(Continued)

(52) U.S. Cl.
CPC ......... *G01N 35/0092* (2013.01); *C12Q 1/68* (2013.01); *C12Q 1/6806* (2013.01);
(Continued)

(58) Field of Classification Search
CPC ............... G01N 35/0092; G01N 35/04; G01N 35/00693; G01N 35/026; G01N 21/6408;
(Continued)

(56) References Cited

U.S. PATENT DOCUMENTS

2002/0090320 A1* 7/2002 Burow .................... B01L 9/523
  422/64
2008/0280350 A1 11/2008 Moriwaki et al.
(Continued)

FOREIGN PATENT DOCUMENTS

JP    2008-278810 A   11/2008
JP    2012-26987 A    2/2012
(Continued)

OTHER PUBLICATIONS

Rafael M. Gordillo et al., Evaluation of the COBAS TaqMan 48 Real-Time PCR System for Quantitation of Hepatitis B Virus DNA, Journal of Clinical Microbiology, Jul. 2005, pp. 3504-3507, vol. 43, No. 7.
(Continued)

*Primary Examiner* — Michael L Hobbs
(74) *Attorney, Agent, or Firm* — Mattingly & Malur, PC

(57) ABSTRACT

In the past, genetic testing systems for exclusive use were needed due to the difference in type or property of specimens. Therefore, a genetic testing system includes: an extraction unit; an assay preparation unit; a reading unit; a first conveying mechanism for conveying a sample among the extraction unit, the assay preparation unit, and the reading unit; multiple sample loading units which are provided corresponding to at least two units of the extraction unit, the assay preparation unit, and the reading unit; and multiple second conveying mechanisms which are provided corresponding to the multiple sample loading units and convey test samples to the inside of the system from the sample loading units.

11 Claims, 15 Drawing Sheets

(51) Int. Cl.
  *C12Q 1/68* (2018.01)
  *G01N 35/04* (2006.01)
  *G01N 21/64* (2006.01)

(52) U.S. Cl.
  CPC ..... G01N 35/00693 (2013.01); G01N 35/026 (2013.01); G01N 35/04 (2013.01); *G01N 21/6408* (2013.01); *G01N 2035/0094* (2013.01); *G01N 2035/0097* (2013.01); *G01N 2035/00326* (2013.01); *G01N 2035/00702* (2013.01); *G01N 2035/0465* (2013.01)

(58) Field of Classification Search
  CPC . G01N 2035/00326; G01N 2035/0465; G01N 2035/0097; G01N 2035/00702; G01N 2035/0094; C12Q 1/68; C12Q 1/6806
  See application file for complete search history.

(56) References Cited

U.S. PATENT DOCUMENTS

| | | | |
|---|---|---|---|
| 2011/0090066 A1* | 4/2011 | Yamaguchi | G01N 35/00663 340/10.51 |
| 2013/0121881 A1 | 5/2013 | Ishizawa et al. | |
| 2013/0130229 A1 | 5/2013 | Sugiyama et al. | |
| 2013/0224753 A1 | 8/2013 | Ishizawa et al. | |
| 2013/0230908 A1 | 9/2013 | Shoji et al. | |
| 2014/0093947 A1 | 4/2014 | Maeda et al. | |

FOREIGN PATENT DOCUMENTS

| | | |
|---|---|---|
| JP | 2012-075413 A | 4/2012 |
| JP | 2012-100549 A | 5/2012 |
| WO | 2012/011379 A1 | 1/2012 |
| WO | 2012/063736 A1 | 5/2012 |
| WO | 2012/176596 A1 | 12/2012 |

OTHER PUBLICATIONS

Ming Chang et al., Validation for Clinical Use of a Novel HIV-2 Plasma RNA Viral Load Assay Using the Abbott m2000 Platform, J. Clin. Virol, Oct. 2012; 55(2): 128-33.

Teresa Spanu et al., Evaluation of the New NucliSENS EasyQ KPC Test for Rapid Detection of *Klebsiella pneumoniae* Carbapenemase Genes (blaKPC), Journal of Clinical Microbiology, Aug. 2012, pp. 2783-2785, vol. 50, No. 8.

Shan Lu et al., Different real-time PCR systems yield different gene expression values, Molecular and Cellular Probe, ( 2010), 1-6.

International Search Report of PCT/JP2013/084040.

* cited by examiner

[FIG. 1-1]
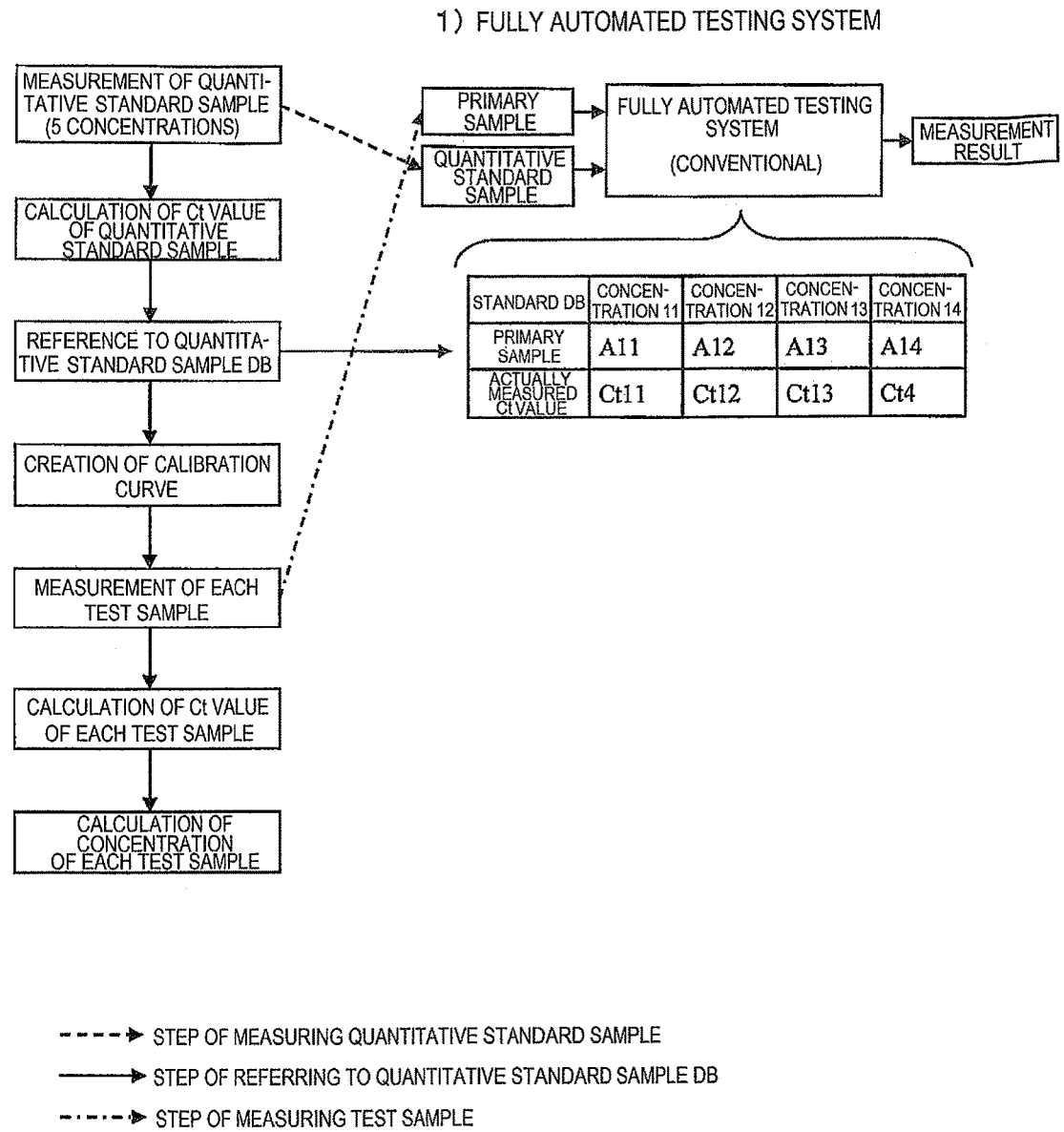
PRIOR ART

[FIG. 1-2]
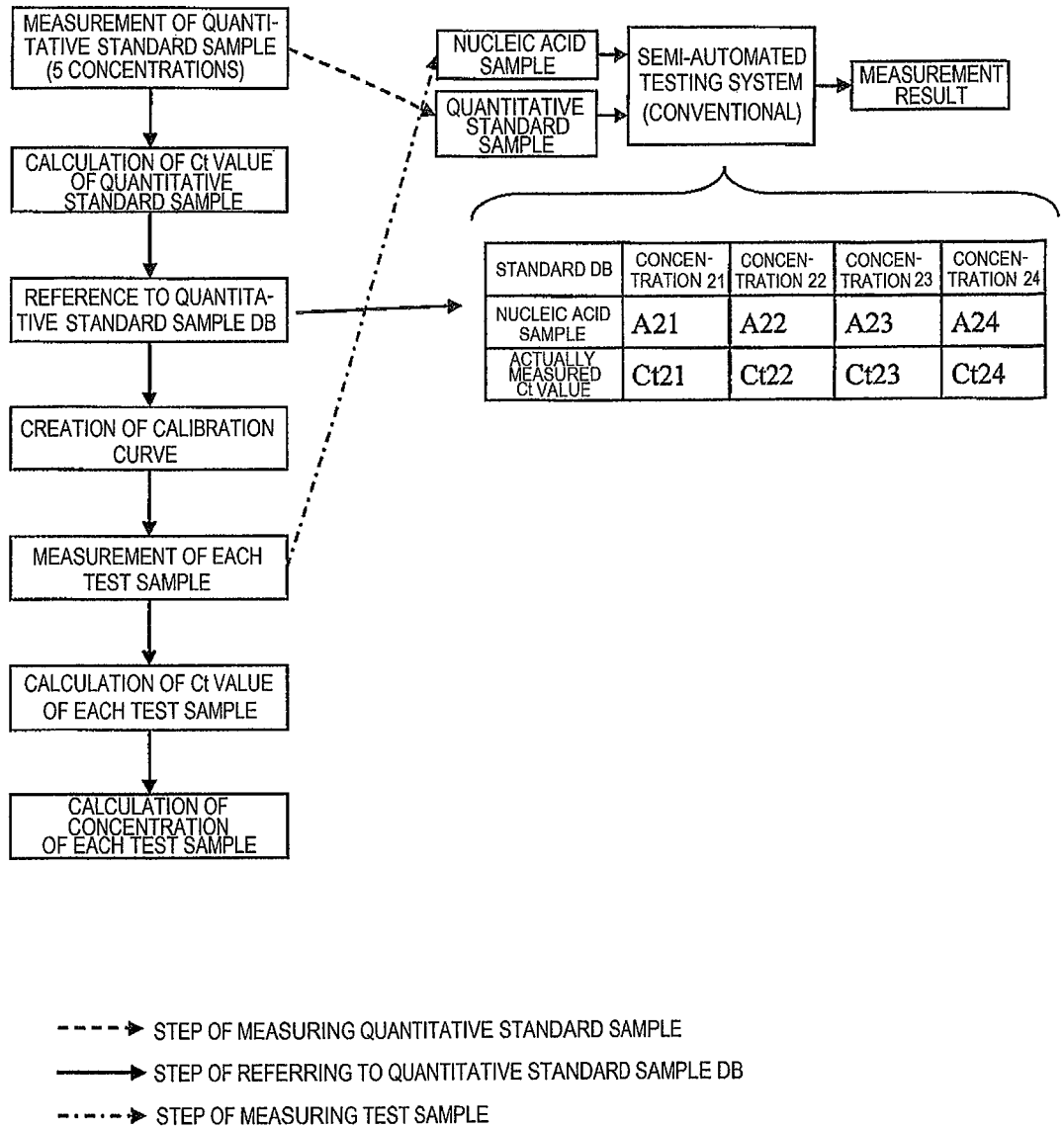
- - - ▶ STEP OF MEASURING QUANTITATIVE STANDARD SAMPLE
⎯⎯▶ STEP OF REFERRING TO QUANTITATIVE STANDARD SAMPLE DB
— · — ▶ STEP OF MEASURING TEST SAMPLE
PRIOR ART

[FIG. 1-3]
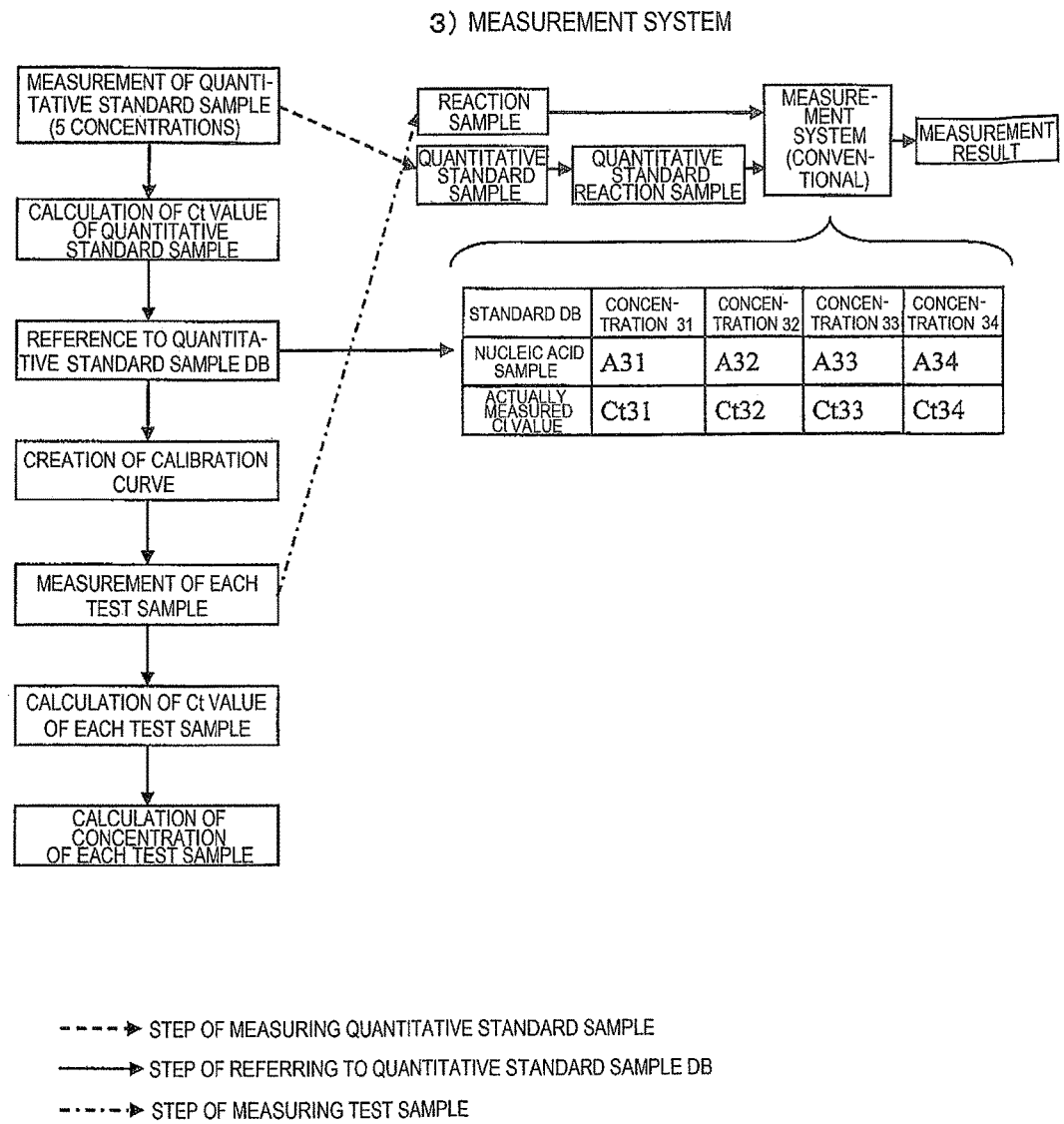
- - - ▶ STEP OF MEASURING QUANTITATIVE STANDARD SAMPLE
———▶ STEP OF REFERRING TO QUANTITATIVE STANDARD SAMPLE DB
— · — · ▶ STEP OF MEASURING TEST SAMPLE
PRIOR ART

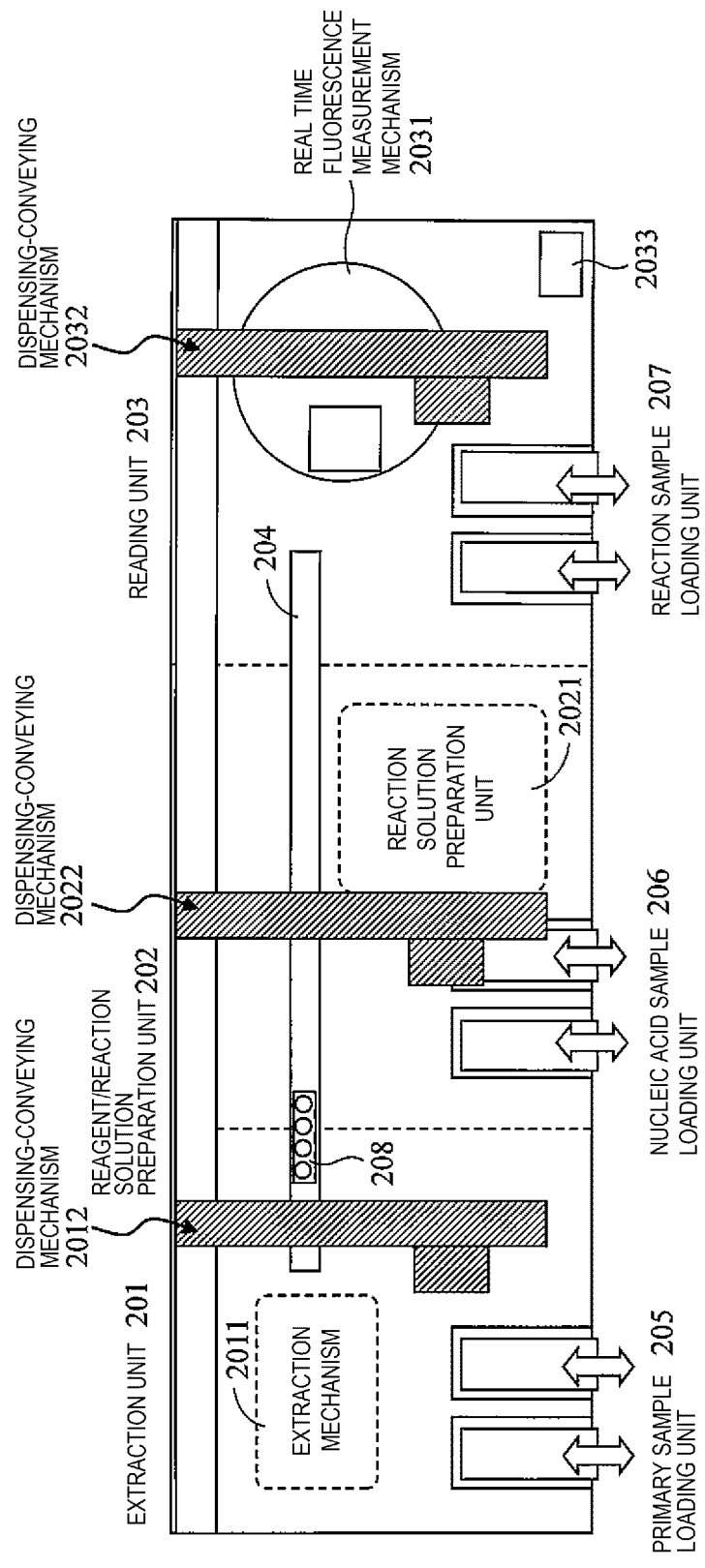

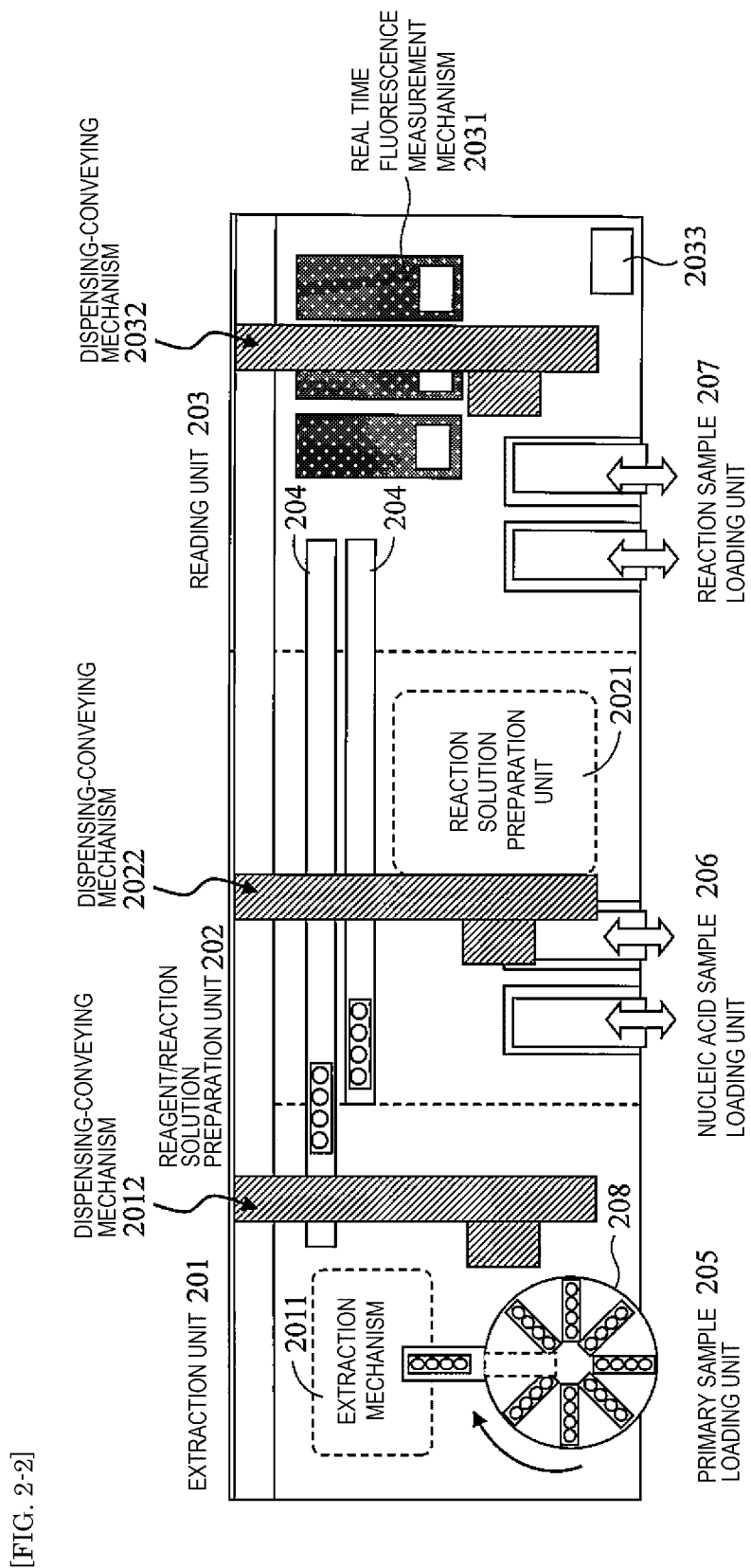

[FIG. 3-1]
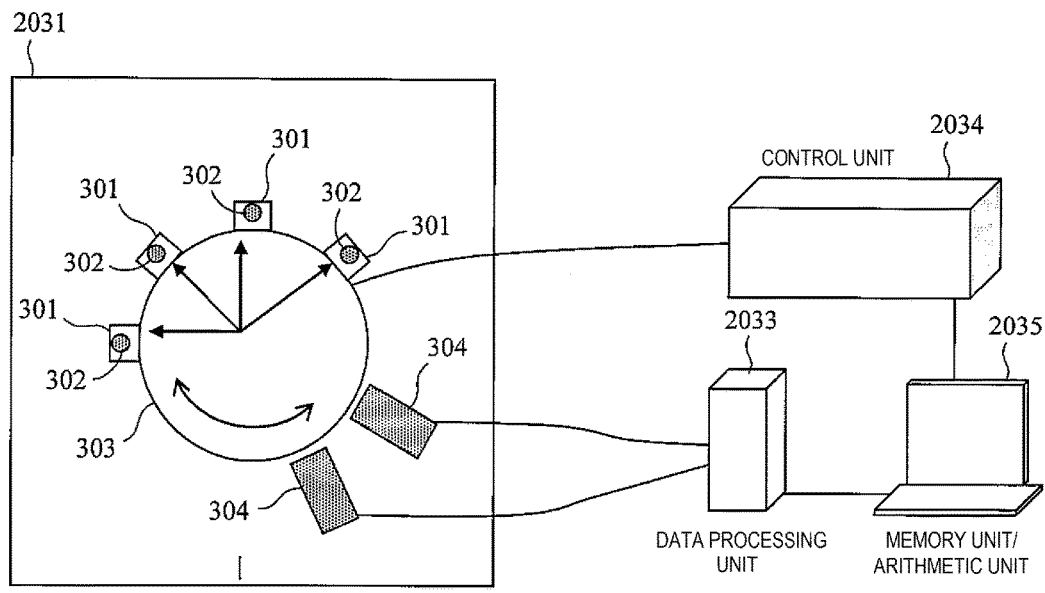
[FIG. 3-2]
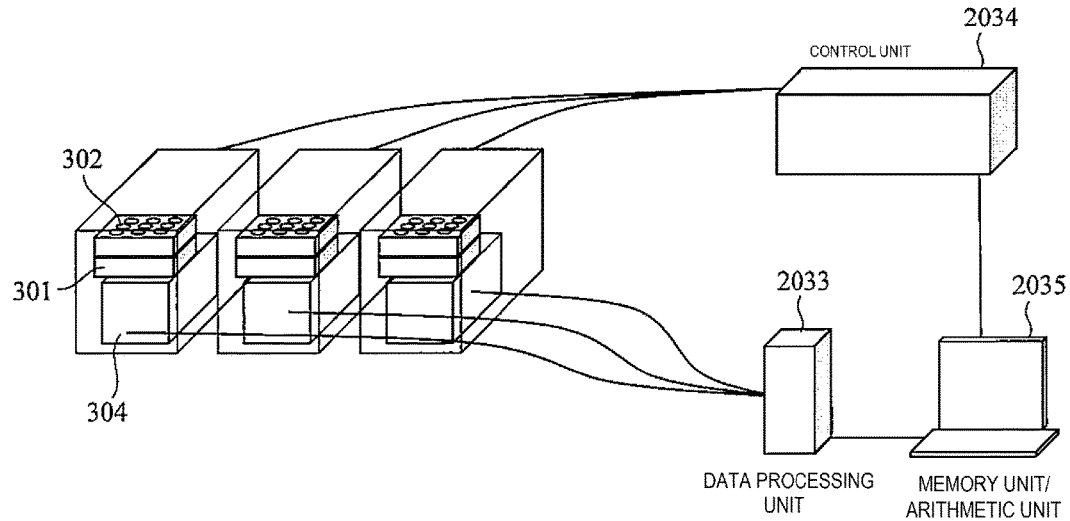

[FIG. 4-1]
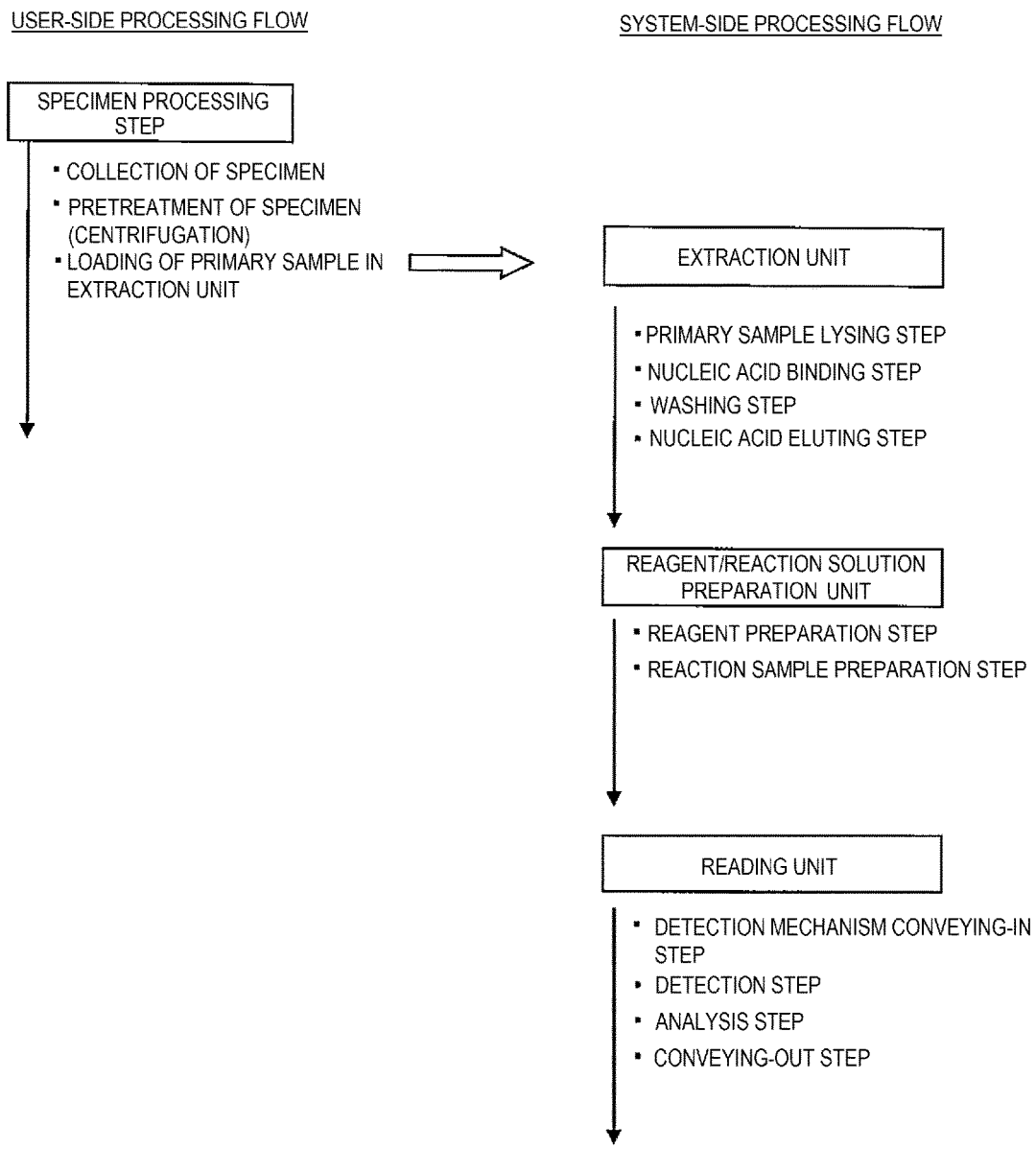

[FIG. 4-2]
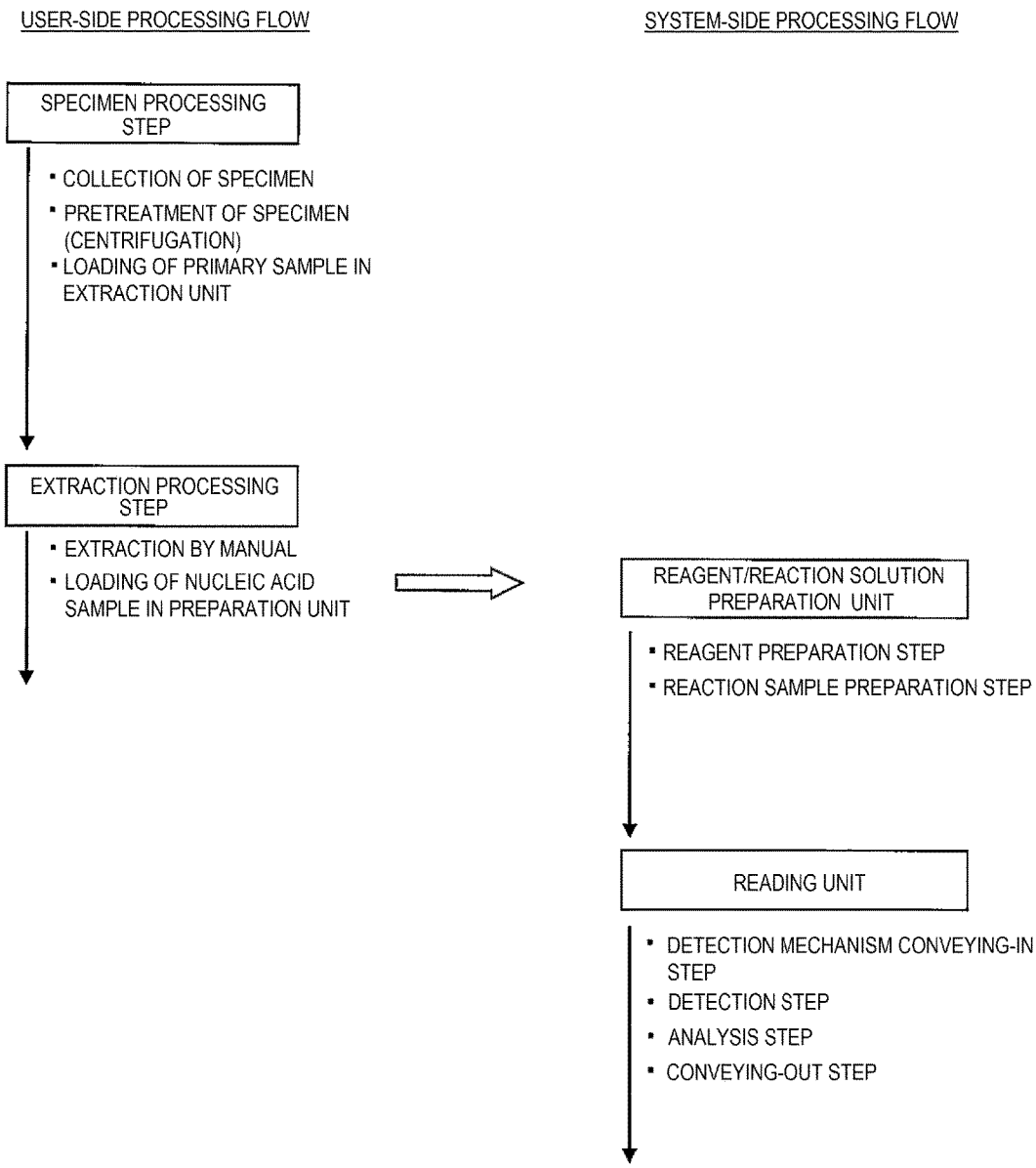

[FIG. 4-3]
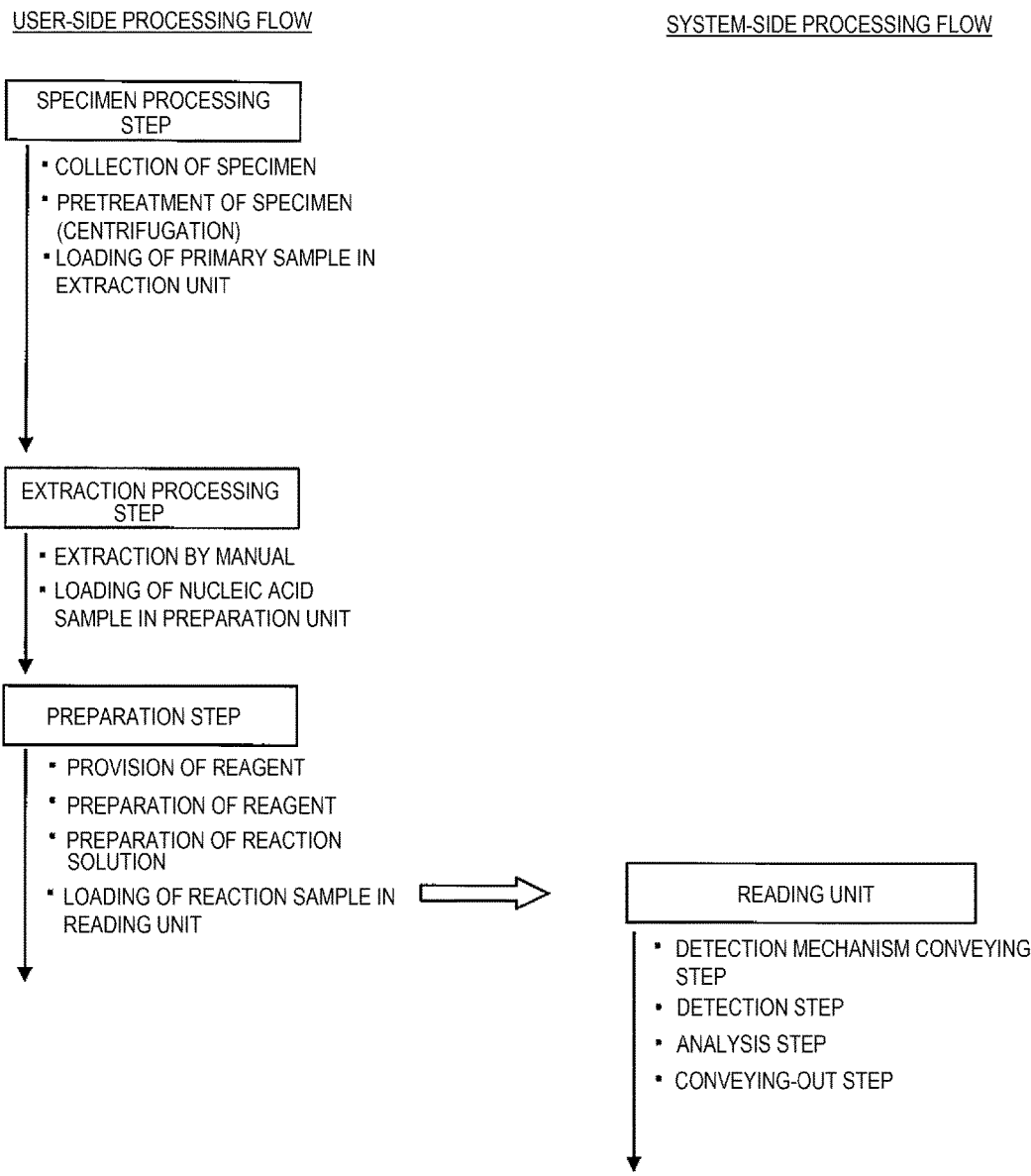

[FIG. 4-4]
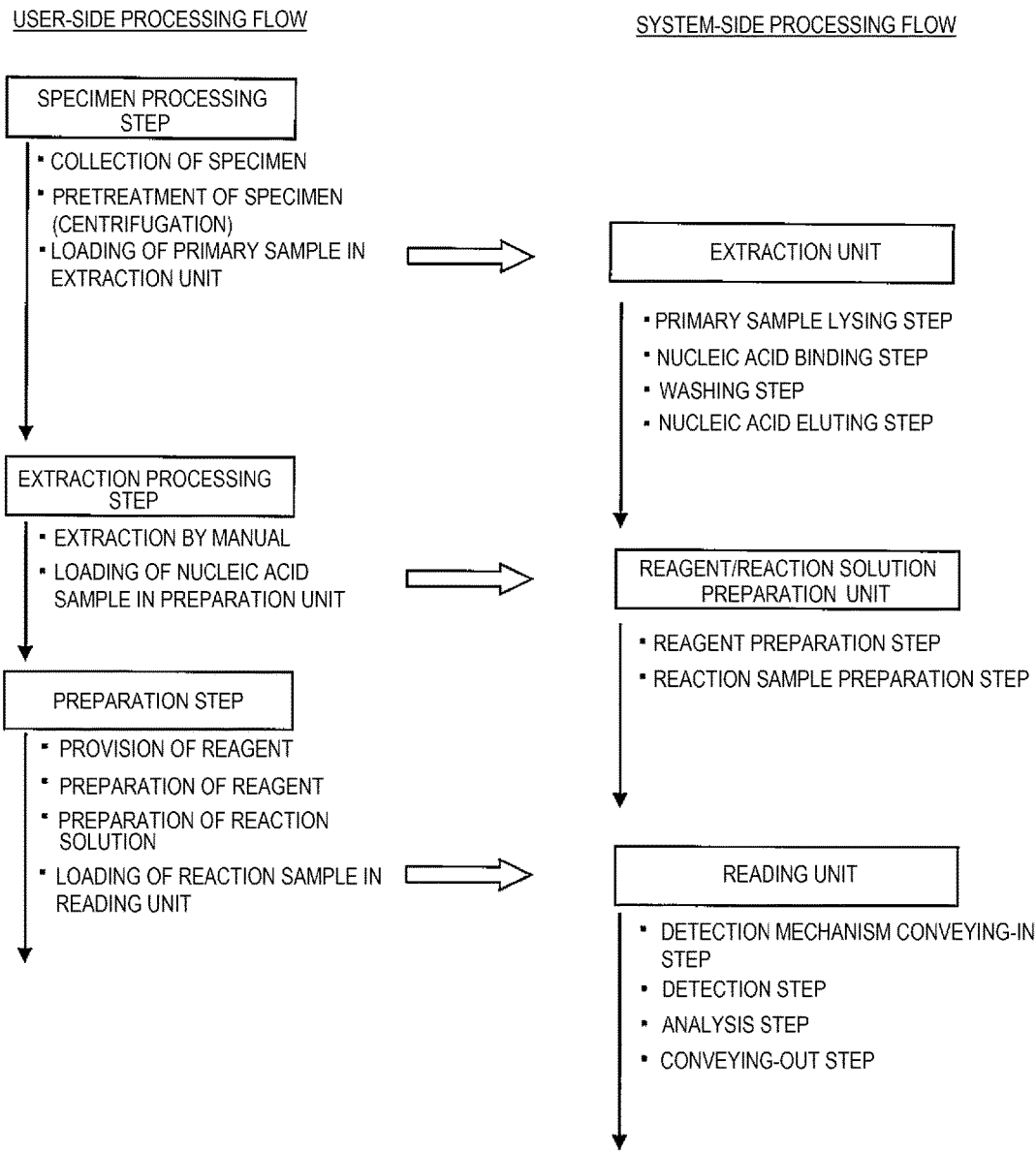

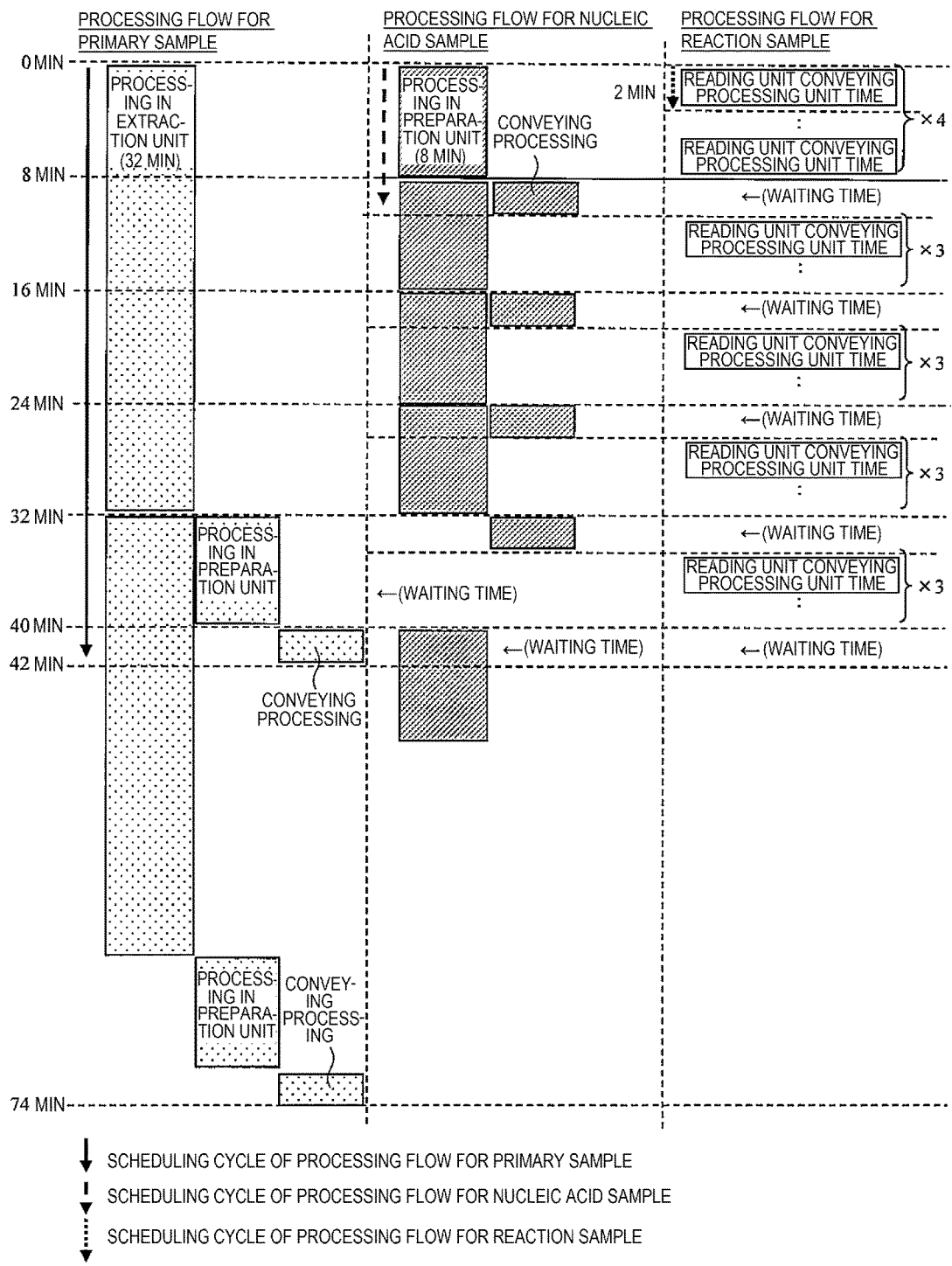
[FIG. 5-1]

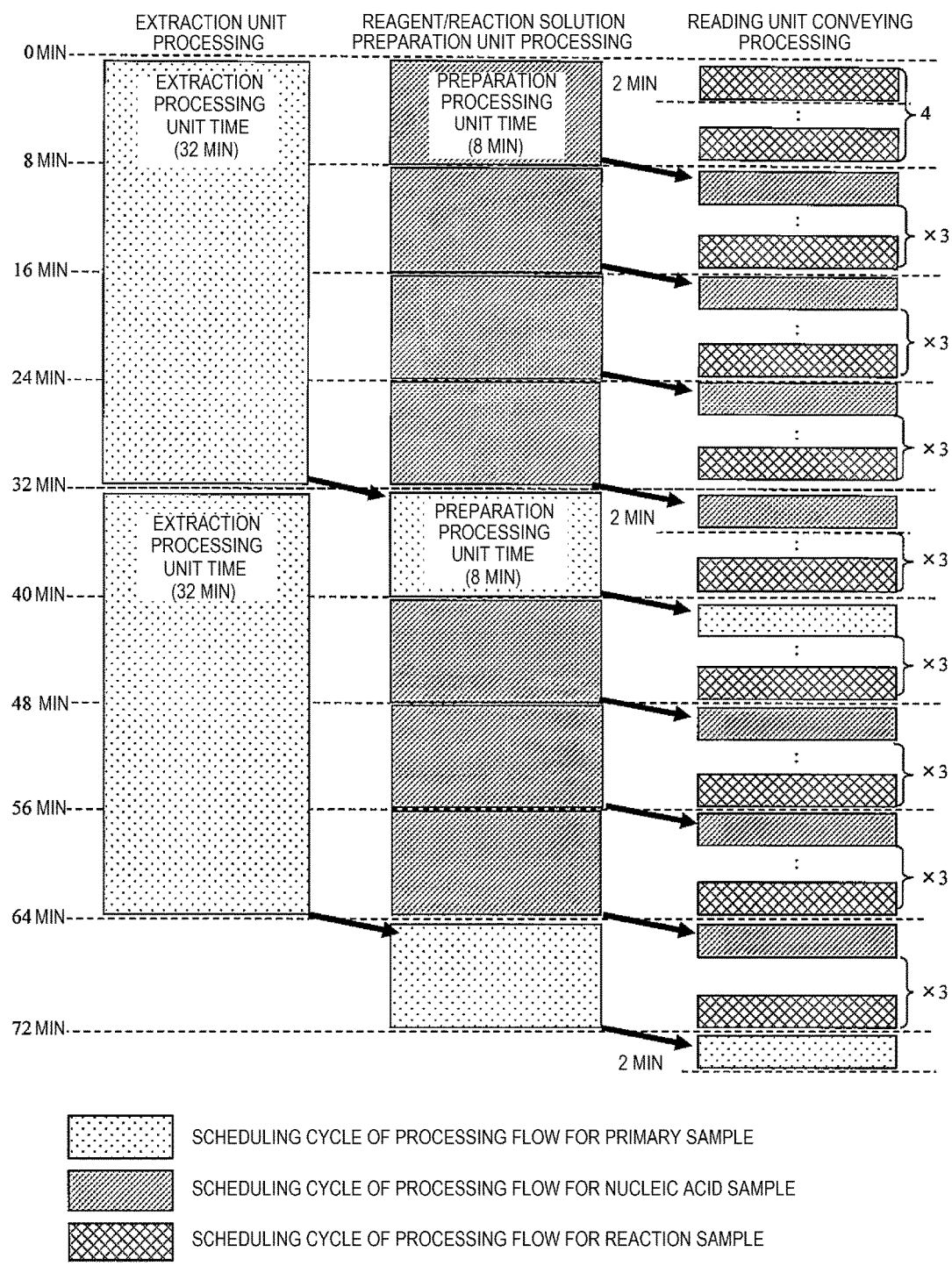
[FIG. 5-2]

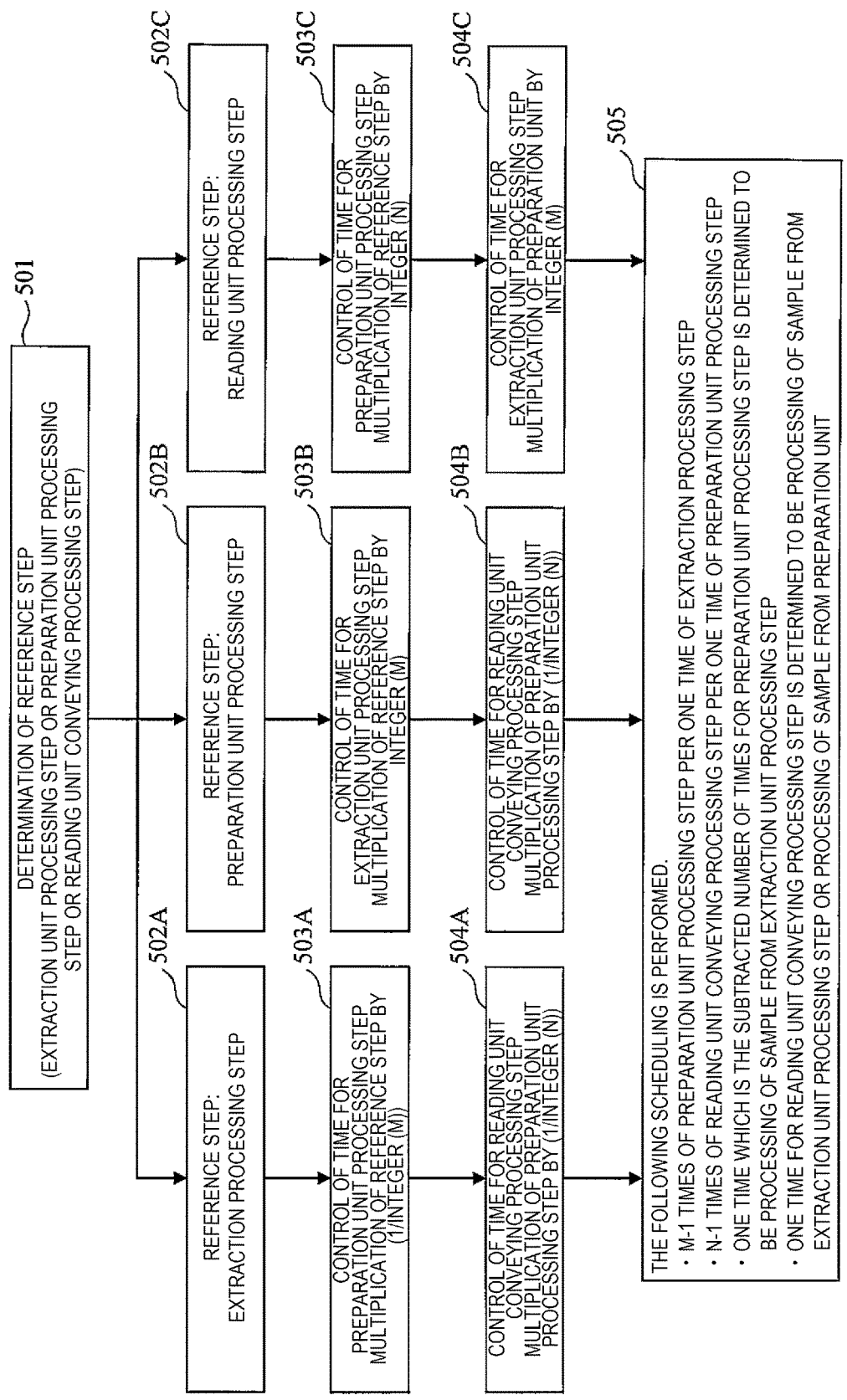

[FIG. 6-1]
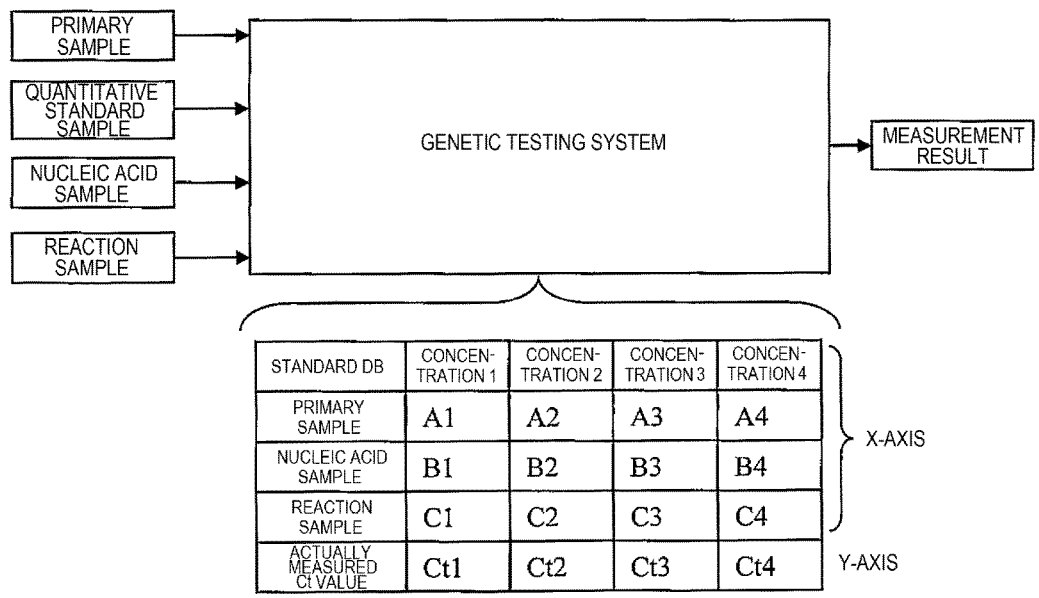

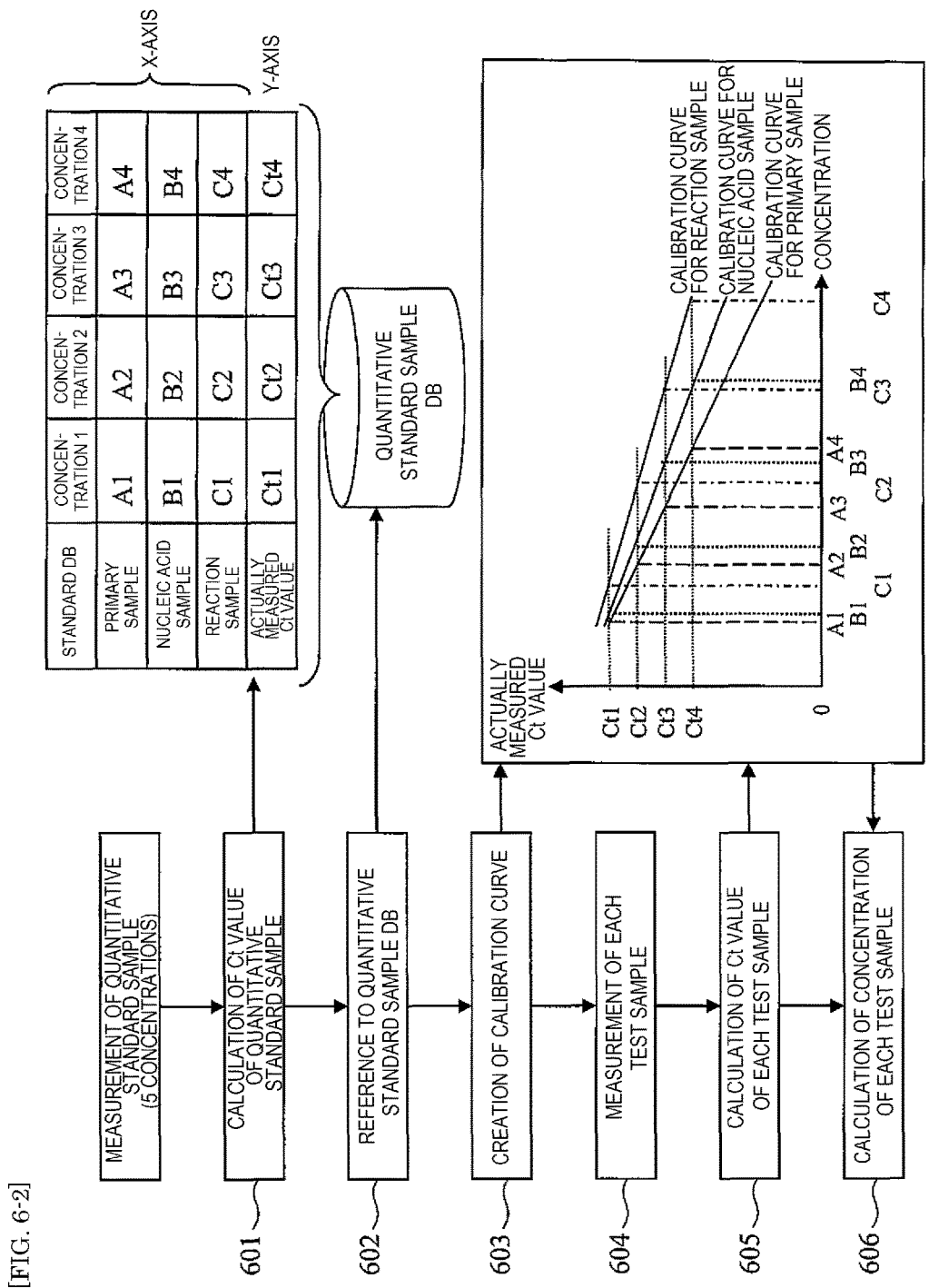
[FIG. 6-2]

GENETIC TESTING DEVICE, GENETIC TESTING METHOD AND PROGRAM

TECHNICAL FIELD

The present invention relates to a genetic testing system, a genetic testing method, and a program.

BACKGROUND ART

Heretofore, a genetic testing system (Cobas TaqMan Auto) which performs a measurement step including nucleic acid extraction in a fully automated manner is provided by Roche, Inc. (see NPL 1). This system is configured such that when a operator dispenses a sample (serum or plasma) into a sample container for exclusive use, sets the container in the system, and gives a command to start a test to the system, the system quantitatively measures the presence or absence of a virus or the like in the sample in a fully automated manner using a real time PCR (Polymerase Chain Reaction) method.

Also from Abbott, Inc., a fully automated genetic testing system (m2000p) is provided (see NPL 2). This system is configured such that when a operator sets a blood collection tube in the system and gives a command to start a test to the system, the system performs procedures from nucleic acid extraction to preparation of a measurement reaction solution in a fully automated manner. Subsequently, when the operator sets the prepared measurement reaction solution in a measurement system for exclusive use and gives a command to start a quantitative determination to the measurement system, the measurement system performs quantitative measurement by a real time PCR method.

These systems can perform all the steps in a fully automated manner, and therefore can reduce the burden on a operator.

Incidentally, from Roche, Inc., also a semi-automated testing system (Cobas Amplicor) which does not include an extraction function shown in NPL 1 is provided. This system is configured such that when a operator extracts nucleic acids by manual and installs a purified nucleic acid sample in the system, the system performs a qualitative test by a PCR method. This system does not include an extraction function, but can receive a nucleic acid sample extracted by manual, and therefore can be applied to a wide range of testing items.

Further, among conventional systems, there are also genetic testing systems (for example, EasyQ (BioMerieuex, Inc.) and ABI 7500 system (Life Technologies, Inc.)), which do not include an extraction function and a preparation function, and perform only measurement. Such a system is configured such that when a operator performs nucleic acid extraction and preparation of a reagent and a reaction solution by manual and sets the prepared measurement reaction solution in the measurement system, the system performs only a real time measurement. In the case of using such a system, since the preparation of a reagent is performed by manual, a wide range of reagent preparation methods can be applied, and thus, various testing items can be mounted.

On the other hand, a quantitative assay for nucleic acids in a sample in a genetic test differs depending on a nucleic acid amplification assay. For example, in the case of using a real time PCR method as the nucleic acid amplification assay, multiple concentration series of quantitative standard samples having known concentrations (hereinafter referred to as "standard series") are measured by a real time PCR method and a calibration curve is created from the measurement results (Ct values) of the quantitative standard samples in advance, and at the time of measurement of a sample having an unknown concentration, the concentration is quantitatively determined by fitting the result of the measured Ct value to the created calibration curve.

Here, the quantitative standard sample includes a quantitative standard sample in which a nucleic acid having a target sequence is mixed in serum or plasma (hereinafter referred to as "quantitative standard sample before extraction") and a purified nucleic acid prepared so as to contain a purified (pseudo) viral nucleic acid at a given concentration (hereinafter referred to as "purified quantitative standard sample").

For reference, in FIGS. 1-1 to 1-3, concepts of the concentration measurement operations in the respective conventional systems described above are shown. FIG. 1-1 shows a concept of processing of a fully automated testing system, FIG. 1-2 shows a concept of processing of a semi-automated testing system, and FIG. 1-3 shows a concept of processing of a measurement system. As shown in FIGS. 1-1 to 1-3, it is found that a sample to be set in the system and a database to be prepared for the system differ depending on the type of the testing system. In particular, for a test which differs in an extraction method, it is necessary to individually provide a quantitative standard sample according to the extraction method. It is because when the extraction method differs, a Ct value to be measured also differs, and therefore, a standard series having a concentration series according to the extraction method is needed. Further, in the case of using an isothermal amplification assay as the nucleic acid amplification assay, a method in which an amplification curve is measured over time in the same manner as a real time PCR method, and an amplification rising time is employed is generally used. That is, multiple samples having known concentrations are prepared as quantitative standard samples, and measurement of the samples is performed in advance, whereby a calibration curve is created, and an amplification rising time of a test sample is fitted to the calibration curve, whereby a sample concentration is determined.

CITATION LIST

Non Patent Literature

NPL 1: JOURNAL OF CLINICAL MICROBIOLOGY, July 2005, p. 3504-3507

NPL 2: J. Clin. Virol. 2012 October; 55(2): 128-33, Epub 2012 Jul. 24

NPL 3: J. Clin. Microbiol. 2012 August; 50(8): 2783-5, Epub 2012 May 23

NPL 4: Mol. Cell Probes. 2010 October; 24(5): 315-20, Epub 2010 Apr. 21

SUMMARY OF INVENTION

Technical Problem

The conventional fully automated testing system is configured such that after a specimen is set, all the previously determined testing operations proceed automatically. However, there are some cases where a predetermined testing operation cannot be applied depending on the type or property of a primary sample. That is, for a fully automated testing system, there exist an applicable genetic test and an inapplicable genetic test. In the case where a specimen is inapplicable to the fully automated testing system, a operator needs to use another genetic testing system (other than the fully automated testing system). Here, the specimen type is, for example, serum or plasma in the case of a genetic test for measuring a virus concentration in the blood, and is sputum in the case of testing bacteria or the like for respiratory system infection. Further, other specimen types include tissues and urine.

For example, there exist fully automated genetic testing systems applicable to serum or plasma, however, there exist a few fully automated testing systems applicable to sputum or tissues. Therefore, in the case of using sputum or tissues as a specimen, a operator needs to extract nucleic acids by manual and perform a test using another genetic testing system.

Incidentally, even if the specimen type is serum or plasma, in the case where the property of the specimen is inapplicable to the fully automated testing system (for example, in the case where the specimen has a high viscosity so that it is difficult to dispense a sample), a operator needs to extract nucleic acids by manual and perform a measurement using another genetic testing system. In this case, for example, even if the primary samples are obtained from the same patient, the measurement is periodically performed using a different genetic testing system, and therefore, there is a problem that the testing results for the same item may vary among the testing systems. In particular, in the case where different testing systems are used due to the difference in property in the same patient, there is a problem in compatibility of the testing results.

Further, in the case of using different multiple types of testing systems, it is necessary to prepare quantitative standard samples to be used when performing quantitative determination of nucleic acids for each testing system, and therefore, there is also a problem that the measurement cost for the quantitative standard samples is increased.

Accordingly, the invention provides a genetic testing system which receives an applicable sample from an arbitrary testing step corresponding to the type or property of a specimen, and can automatically perform the subsequent testing step for any sample.

Solution to Problem

In order to achieve the above object, the invention includes an extraction unit, an assay preparation unit, a reading unit, a first conveying mechanism for conveying a sample among the extraction unit, the assay preparation unit, and the reading unit, multiple sample loading units which are provided corresponding to at least two units of the extraction unit, the assay preparation unit, and the reading unit, and multiple second conveying mechanisms which are provided corresponding to the multiple sample loading units and convey test samples to the inside of the system from the sample loading units.

Advantageous Effects of Invention

According to the invention, regardless of the difference in the type or property of a specimen, a genetic test using one genetic testing system can be performed so that compatibility of the testing results can be ensured. The object, configuration, and effect other than those described above are clarified by the description of the following embodiments.

BRIEF DESCRIPTION OF DRAWINGS

FIG. 1-1 is a view showing a concept of processing of a conventional fully automated testing system.

FIG. 1-2 is a view showing a concept of processing of a conventional semi-automated testing system.

FIG. 1-3 is a view showing a concept of processing of a conventional measurement system.

FIG. 2-1 is a view illustrating a first configuration example of a genetic testing system according to an embodiment.

FIG. 2-2 is a view illustrating a second configuration example of the genetic testing system according to the embodiment.

FIG. 3-1 is a view illustrating a first configuration example of a real time fluorescence measurement mechanism and peripheral devices thereof.

FIG. 3-2 is a view illustrating a second configuration example of the real time fluorescence measurement mechanism and peripheral devices thereof.

FIG. 4-1 is a view illustrating a testing process to be performed when a primary sample is loaded.

FIG. 4-2 is a view illustrating a testing process to be performed when a nucleic acid sample is loaded.

FIG. 4-3 is a view illustrating a testing process to be performed when a reaction sample is loaded.

FIG. 4-4 is a view illustrating a testing process to be performed when a primary sample, a nucleic acid sample, and a reaction sample are loaded in corresponding sample loading units, respectively.

FIG. 5-1 is a view illustrating a scheduling cycle example of a processing flow for each sample.

FIG. 5-2 is a view illustrating a scheduling cycle example for each processing unit.

FIG. 5-3 is a view illustrating a processing procedure for determining a reference step.

FIG. 6-1 is a conceptual view of a concentration calculation step based on quantitative standard samples.

FIG. 6-2 is a view illustrating the concentration calculation step based on quantitative standard samples.

DESCRIPTION OF EMBODIMENTS

Hereinafter, embodiments of the invention will be described with reference to the drawings. Incidentally, the embodiments of the invention are not limited to the configuration examples described below and various modifications can be made within the scope of the technical idea thereof. In the following description, a genetic test includes (1) a real time PCR method, (2) an isothermal amplification assay (a LAMP assay, a NASBA assay, or a TRC assay), (3) a sequence analysis method such as a Sanger method, (4) an expression analysis method, (5) a method capable of detecting a gene sequence, a mutation, SNPs, nucleic acid modification, etc., and a difference in the testing method is by no means limited to the invention proposed in this description.

(1) Configuration of Genetic Testing System (1-1) Overall Configuration

In the following embodiments, a genetic testing system which can perform a fully automated genetic test for some specimens, and can perform a semi-automated genetic test for a nucleic acid sample extracted by manual or a reaction sample prepared by manual for some specimens will be described. That is, a genetic testing system which is applicable to the genetic tests by one system regardless of the type or property of a specimen. Therefore, the genetic testing system according to the embodiment is configured such that a nucleic acid sample extracted by manual or a reaction sample prepared by manual can be received from an arbitrary testing step. In other words, a genetic testing system which can perform the subsequent processing step equally regardless of the difference in the processing step in which the sample is received, and also can obtain testing results according to the step in which the sample is loaded will be described. Further, in the following embodiments, a genetic testing system mounted with a control function (program) for processing samples for which the processing steps are different simultaneously (in a parallel manner) will also be described.

FIGS. 2-1 and 2-2 show configuration examples of a genetic testing system 200 according to this embodiment. The genetic testing system 200 according to the embodiment is constituted by the following three testing units: an extraction unit 201; a reagent/reaction solution preparation unit 202; and a reading unit 203 corresponding to individual testing steps, sample loading units for loading a container which can be received by each testing unit and encloses a sample in the system, and a conveying mechanism 204 for conveying the container among the testing units. In this description, the sample loading unit corresponding to the extraction unit 201 is referred to as a primary sample loading unit 205, the sample loading unit corresponding to the reagent/reaction solution preparation unit 202 is referred to as a nucleic acid sample loading unit 206, and the sample loading unit corresponding to the reading unit 203 is referred to as a reaction sample loading unit 207. Incidentally, the system may be configured to include only arbitrary two sample loading units among these three sample loading units.

(1-2) Configuration of Respective Units (1-2-1) Configuration of Extraction Unit The extraction unit 201 is constituted by a dispensing mechanism for dispensing a nucleic acid extraction reagent into a container enclosing a primary sample, a container conveying mechanism for conveying the container in the unit, an extraction mechanism 2011 for extracting nucleic acids from the primary sample, and a primary sample loading unit 205. Hereinafter, an integral mechanism of the dispensing mechanism and the container conveying mechanism is referred to as a dispensing-conveying mechanism 2012.

The extraction mechanism 2011 may have any configuration as long as it can lyse a primary sample and purify (extract) nucleic acids in the primary sample. The extraction mechanism 2011 includes, for example, a device for extracting nucleic acids by allowing the lysed primary sample to pass through a column packed with a nucleic acid binding carrier in the form of a filter. A method of allowing a liquid to pass through the column includes a method of using a centrifuge and a method of applying pressure with a syringe. The nucleic acid binding carrier includes magnetic particles coated with silica, and a method of collecting the magnetic particles with a magnet and the like are used.

The container conveying mechanism is a mechanism for conveying a sample container in which nucleic acids are extracted in the nucleic acid extraction step in the same unit. However, the container conveying mechanism may be mounted with a function of conveying the container to the reagent/reaction solution preparation unit 202, which is the testing unit at the next stage. Incidentally, in the case where the extraction sample is conveyed in the form of a liquid, the extraction mechanism 2011 may also have the conveying function of the container conveying mechanism. In this manner, a system configuration in which the container conveying mechanism is not provided may also be considered.

The primary sample loading unit 205 has a mechanism capable of installing and loading a container (for example, a blood collection tube) enclosing a primary sample. For example, as shown in FIG. 2-1, a configuration in which two or more conveying lanes for loading a container enclosing a primary sample in the system are provided may be adopted. FIG. 2-1 shows a case where two conveying lanes are provided. In this case, while the system is accessing a first conveying lane, a operator can access a second conveying lane. Incidentally, in the case where the container enclosing a primary sample is a blood collection tube, it is desirable that an identifier (ID) of the primary sample can be recognized when the blood collection tube is loaded in each conveying lane.

Alternatively, the primary sample loading unit 205 may be a rotary drive-type disk mechanism as shown in FIG. 2-2. In this case, in the disk mechanism, a conveying lane for drawing a sample rack 208 in the extraction mechanism 2011 is radially disposed around the rotation axis. In the case of this system configuration, also during the extraction processing by the system, a operator can load the container enclosing a primary sample in the system and can replace the container. In the case where the container enclosing a primary sample is a blood collection tube, it is desirable that an identifier (ID) of the primary sample can be recognized when the sample rack 208 is loaded in the conveying lane.

In this description, the primary sample refers to a sample before extracting nucleic acids such as serum, plasma, urine, feces, or sputum. The primary sample to be loaded in the extraction mechanism 2011 may be any as long as nucleic acids can be automatically extracted in the extraction unit 201.

As the extraction reagent to be installed in the extraction unit 201, for example, a set including a lysing reagent for lysing protein components, a binding reagent for facilitating binding of nucleic acids to the nucleic acid binding carrier by depositing the nucleic acids, a washing reagent for washing off contaminants bound to the binding carrier, and an eluent reagent for eluting the nucleic acids from the nucleic acid binding carrier is generally used. The respective reagent components vary, however, in the invention, any extraction reagent may be used as long as it can extract nucleic acids in the extraction unit.

In the extraction unit 201, as expendable members, a dispensing chip for dispensing a sample or a reagent, a carrier for binding nucleic acids thereto, a container for receiving a sample, and the like are used. These members may be selected so as to form a most suitable configuration according to an extraction method.

(1-2-2) Configuration of Reagent/Reaction Solution Preparation Unit

The reagent/reaction solution preparation unit 202 is constituted by a dispensing mechanism for dispensing a reagent into a container enclosing a nucleic acid sample, a container conveying mechanism for conveying the container in the unit, a reagent installing unit, a reaction solution preparation unit 2021, and a nucleic acid sample loading unit 206. Hereinafter, an integral mechanism of the dispensing mechanism and the container conveying mechanism is referred to as a dispensing-conveying mechanism 2022.

In the reaction solution preparation unit 2021, for example, a mechanism for preparing a master mix from an installed reagent, a mechanism for preparing a nucleic acid sample and the master mix, and according to the requirement for a genetic testing method to be mounted, a stirring mechanism, a capping mechanism, a heating mechanism, etc. are disposed.

For example, in the case where the genetic testing method mounted on the system is a NASBA method and a TRC method, in order to perform a quantitative measurement, it is important that a reaction temperature is reached when an enzyme is added, and therefore, a heating mechanism is disposed in the reaction solution preparation unit 2021.

Further, for example, in the case where the genetic testing method mounted on the system is a real time PCR method, control of the temperature is performed after every preparation of a reaction solution, and therefore, it is not necessary to provide a heating mechanism in the reaction solution preparation unit 2021. In this case, the reaction solution preparation unit 2021 may have any configuration as long as a reaction solution can be prepared from a nucleic acid sample.

The nucleic acid sample loading unit 206 has a mechanism capable of installing and loading a container enclosing a nucleic acid sample. For example, as shown in FIG. 2-1, a configuration in which two or more conveying lanes for loading a container enclosing a nucleic acid sample in the system are provided may be adopted. FIG. 2-1 shows a case where two conveying lanes are provided. In this case, while the system is accessing a first conveying lane, a operator can access a second conveying lane. Incidentally, a bar code label is attached to the container enclosing a nucleic acid sample, and it is desirable that an identifier (ID) of the nucleic acid sample can be recognized when the container is loaded in each conveying lane. Incidentally, also the nucleic acid sample loading unit 206 may be a rotary drive-type disk mechanism in the same manner as the primary sample loading unit 205.

In this description, the nucleic acid sample refers to nucleic acids extracted by manual by a operator, nucleic acids purified using another automated nucleic acid extraction system, a quantitative standard sample of purified nucleic acids, or the like. The nucleic acid sample to be loaded in the reaction solution preparation unit 2021 may be any as long as it is a sample in the form of purified nucleic acids to undergo an analysis.

The reagent to be installed in the reagent/reaction solution preparation unit 202 is any as long as it can perform a genetic test of a sample extracted in the extraction unit 201 or a nucleic acid sample installed in the reagent/reaction solution preparation unit 202. Preferably, it is desirable that two or more types of testing reagents can be installed so that different items can be tested by a test for a nucleic acid sample conveyed from the extraction unit 201 and a test for a nucleic acid sample loaded from the nucleic acid sample loading unit 206. More preferably, it is desirable that six or more types of reagents can be installed so that an operation with high flexibility in the reading section 203, which will be described below, can be performed.

In the reagent/reaction solution preparation unit 202, as expendable members, a dispensing chip for dispensing a sample or a reagent, a reagent preparation container, a reaction container, and the like are used. These members may be selected so as to form a most suitable configuration according to each amplification assay.

(1-2-3) Configuration of Reading Unit

The reading unit 203 is constituted by a dispensing mechanism for dispensing a reagent into a container enclosing a nucleic acid sample, a container conveying mechanism for conveying the container in the unit, a real time fluorescence measurement mechanism 2031, a data processing unit 2033 which processes fluorescence measurement data, and a reaction sample loading unit 207. Hereinafter, an integral mechanism of the dispensing mechanism and the container conveying mechanism is referred to as a dispensing-conveying mechanism 2032. Here, the real time fluorescence measurement mechanism 2031 desirably has a functional mechanism capable of receiving a reaction sample to be conveyed at a different timing. Incidentally, the real time fluorescence measurement mechanism 2031 is one example, and any detection mechanism can be used as long as it can measure the reaction sample.

In FIGS. 3-1 and 3-2, configurations of the real time fluorescence measurement mechanism 2031 and peripheral devices thereof are shown. Incidentally, a difference between FIG. 3-1 and FIG. 3-2 is a device configuration of the real time fluorescence measurement mechanism 2031. In the device configuration shown in FIG. 3-1, temperature control blocks 301 and reaction containers 302 correspond in a one-to-one manner, and the temperature of the reaction containers 302 are controlled individually. In the device configuration shown in FIG. 3-2, temperature control blocks 301 and reaction containers 302 correspond in a one-to-many manner, and the temperatures of multiple reaction containers 302 are controlled collectively.

The reaction container 302 may be formed from any material and may have any shape as long as the material transmits a fluorescence wavelength and conducts heat of the temperature control block 301. As the reaction container 302, for example, a PCR tube (Greiner, Inc., Germany) free of DNase or RNase, a container having a porous structure and including reaction wells, or the like can be used.

In the case of the real time fluorescence measurement mechanism 2031 shown in FIG. 3-1, the temperature control blocks 301 are arranged along the outer periphery of a rotary disk 303. The real time fluorescence measurement mechanism 2031 detects fluorescence from the reaction container 302 in real time by a fluorescence detector 304 while changing the temperature of the reaction container 302 installed in the temperature control block 301 within the range from 40° C. to 95° C. The fluorescence detector 304 is fixedly disposed on the outer side of the rotary disk 303, and detects fluorescence from the reaction container 302 passing through the front thereof accompanying the rotation of the rotary disk 303. Incidentally, the temperature control blocks 301 can individually control the temperature.

The temperature control blocks 301 may be arranged on the outer periphery of a fixed disk in place of the rotary disk 303. In this case, a mechanism of moving the fluorescence detector 304 along the outer periphery of the fixed disk may be adopted. In this case, the fluorescence detector 304 detects fluorescence from the reaction container 302 installed in the temperature control block 301 passing through the front thereof.

In the case of the real time fluorescence measurement mechanism 2031 shown in FIG. 3-2, the multiple temperature control blocks 301, each of which collectively controls the temperatures of the multiple reaction containers 302, are disposed in parallel with one another. In the case of this configuration, the fluorescence detector 304 is disposed on a lower side of each of the temperature control blocks 301. Incidentally, as for the position where the fluorescence detector 304 is disposed, the fluorescence detector 304 may be placed in the most suitable position according to the detection method.

As described above, the configuration of the real time fluorescence measurement mechanism 2031 varies, however, the control of the temperature may be performed by any method as long as the temperature can be controlled. For example, it is also possible to use an air incubator method in which the control of the temperature is performed by changing the temperature of air.

Incidentally, the temperature of the temperature control block 301 is controlled by a control unit 2034 in the case of the device configuration shown in FIG. 3-1 and also in the case of the device configuration shown in FIG. 3-2. Further, the output of the fluorescence detector 304 is processed by a data processing unit 2033. A memory unit/arithmetic unit 2035 has a quantitative standard sample concentration information database for each testing item. In the concentration information database, concentration information for one set of quantitative standard samples to be used in a given testing item (concentration information corresponding to a primary sample loaded from the primary sample loading unit 205, concentration information corresponding to a nucleic acid sample loaded from the nucleic acid sample loading unit 206, or concentration information corresponding to a reaction sample loaded from the reaction sample loading unit 207) are stored. The data processing unit 2033 selects concentration information to be referred to according to a place where the sample is loaded, and the concentration is calculated based on the selected concentration information and the detection result by the fluorescence detector 304.

The reaction sample loading unit 207 has a configuration capable of installing and loading a container enclosing a reaction sample. For example, as shown in FIG. 2-1, a configuration in which two or more conveying lanes for loading a container enclosing a reaction sample in the system are provided may be adopted. FIG. 2-1 shows a case where two conveying lanes are provided. In this case, while the system is accessing a first conveying lane, a operator can access a second conveying lane. Incidentally, a two-dimensional code label is attached to the container enclosing a reaction sample, and it is desirable that an identifier (ID) of the reaction sample can be recognized when the container is loaded in each conveying lane.

In this description, the reaction sample is a sample in which all materials necessary for the reaction, that is, reagents necessary for the reaction, a nucleic acid sample, and the like are enclosed. The reaction sample may be a reaction sample conveyed from the reagent/reaction solution preparation unit 202 at the previous stage, or may be a reaction sample conveyed from the reaction sample loading unit 207 after preparing the sample by manual by a operator using a micro dispenser, a stirrer, a tabletop centrifuge, and the like. The reaction sample is installed in a state where it is enclosed in a container capable of being installed in the temperature control block 301.

Incidentally, in the case where a reaction sample prepared by manual is loaded in the reading unit 203, the following system flow is preferable. First, when a reaction sample is loaded in the reading unit 203, a operator specifies the identifier (ID) of the reaction sample. Thereafter, the dispensing-conveying mechanism 2032 conveys the reaction container to the real time fluorescence measurement mechanism 2031 and installs the reaction container in the temperature control block 301. The fluorescence detector 304 detects a target nucleic acid by control of the temperature and a detection method suitable for a testing method to be mounted.

(1-3) Processing Operation

Here, processing flows (a user-side processing flow and a system-side processing flow) to be performed by the genetic testing system according to the embodiment will be described. Hereinafter, with respect to the case of measuring a nucleic acid by a real time PCR method, it will be described that the genetic testing system according to the embodiment can perform a genetic test regardless of the type or property of the specimen.

In FIGS. 4-1 to 4-4, testing operation flows in the case of using the genetic testing system according to this embodiment are shown. FIG. 4-1 is a processing flow to be performed in the case where a primary sample is loaded from the primary sample loading unit 205, FIG. 4-2 is a processing flow to be performed in the case where a nucleic acid sample is loaded from the nucleic acid sample loading unit 206, FIG. 4-3 is a processing flow to be performed in the case where a reaction sample is loaded from the reaction sample loading unit 207, and FIG. 4-4 is a processing flow to be performed in the case where a primary sample, a nucleic acid sample, and a reaction sample are loaded in corresponding sample loading units, respectively. Incidentally, the respective processes associated with the respective processing steps or the respective units are known per se, and therefore, a detailed description thereof is omitted.

Hereinafter, a specific example of the processing operation will be described by showing a case where in all the sample loading units of the genetic testing system according to this embodiment, corresponding samples (a primary sample, a nucleic acid sample, and a reaction sample) are simultaneously loaded as an example. Incidentally, in the genetic testing system according to this embodiment, a sample can be loaded in an arbitrary processing unit, and therefore, it is necessary to adjust a processing schedule between the sample and the other sample to be loaded in a different position. The genetic testing system simultaneously starts the processing for each sample group in the order that the test is requested regardless of the difference in the sample loading position.

For example, in the case where 8 primary samples as a primary sample group, 28 nucleic acid samples as a nucleic acid sample group, and 112 reaction samples as a reaction sample group are loaded, the genetic testing system according to this embodiment simultaneously starts the processing for a first requested primary sample in the primary sample group, a first requested sample in the nucleic acid sample group, and a first requested sample in the reaction samples group.

For the primary sample group, the genetic testing system starts a nucleic acid extraction step (a primary sample lysing step, a nucleic acid binding step, a washing step, and a nucleic acid eluting step) by the extraction unit 201. For the nucleic acid sample group, the genetic testing system starts a preparation step (a reagent preparation step and a reaction sample preparation step) by the reagent/reaction solution preparation unit 202. For the reaction sample group, the genetic testing system starts a process for conveying the reaction sample to the real time fluorescence measurement mechanism 2031 by the reading unit 203. The processing timing for the respective types of samples at this time follows the most suitable schedule determined in advance in the genetic testing system. More preferably, it follows a schedule optimized according to a combination of the test samples requested before starting the test.

Hereinafter, the most suitable schedule will be described based on a specific example. In the following description, a one-time processing time in the case where the respective steps are simultaneously performed is defined as a unit time. At this time, a unit time for the extraction step for 4 primary samples is assumed to be 32 minutes, a unit time for the preparation step for 4 nucleic acid samples is assumed to be 8 minutes, and a unit time for the reading unit conveying step for 4 reaction samples is assumed to be 2 minutes. In this case, scheduling is performed such that 148 samples in total including 8 primary samples, 28 nucleic acid samples, and 112 reaction samples are loaded in the real time fluorescence measurement mechanism 2031 in 74 minutes. In this schedule, a control device or a calculating machine (not shown) performs calculation. Incidentally, the schedule is calculated based on the extraction step processing unit time.

In the case of the above-described case, the processing numbers of the respective samples in a first scheduling cycle are represented by the following calculation formulae.

(the number of primary samples)=processing number in one unit time for nucleic acid extraction step (the number of nucleic acid samples)=(unit time for extraction step)/(unit time for preparation step)×(processing number in one unit time for preparation step)

(the number of reaction samples)=(unit time for preparation step)/(unit time for conveying step)×(processing number in one unit time for conveying step)

In a second scheduling cycle and thereafter, as shown in FIGS. 5-1 and 5-2, awaiting time occurs due to an interrupt of the processing result of the upstream step. Incidentally, FIG. 5-1 shows scheduling cycles from the perspective of the samples, and FIG. 5-2 shows scheduling cycles from the perspective of the respective units.

As shown in FIGS. 5-1 and 5-2, in the genetic testing system according to this embodiment, in parallel to extraction of nucleic acids in the primary sample by the extraction unit 201, the reaction sample preparation process for the nucleic acid sample is performed by the reagent/reaction solution preparation unit 202, and simultaneously therewith, a process for conveying the prepared reaction sample in the detection mechanism (real time fluorescence measurement mechanism 2031) is performed.

Incidentally, the genetic testing system according to this embodiment suspends the conveying process for the reaction sample at a timing of conveying the nucleic acid sample, and suspends the preparing process for the nucleic acid sample and the conveying process for the reaction sample at a timing of the preparation process and the conveying process for the primary sample.

The processing numbers of the respective samples in a second scheduling cycle and thereafter are represented by the following calculation formulae.

(the number of primary samples)=processing number in one unit time for nucleic acid extraction step (the number of nucleic acid samples)={(unit time for extraction step)/(unit time for preparation step)−(unit time for preparation step)}×(processing number in one unit time for preparation step)

(the number of reaction samples)={(unit time for preparation step)/(unit time for conveying step)−(unit time for conveying step)}×(processing number in one unit time for conveying step)

By repeating the scheduling cycle, in the genetic testing system according to this embodiment, the previously shown 148 samples (8 primary samples, 28 nucleic acid samples, and 112 reaction samples) can be conveyed in the reading unit 203 in a total processing time of 74 minutes.

It is needless to say that the above-described scheduling cycle is an example. For example, the preparation processing unit time may be determined to be an integer fraction of the extraction processing unit time, and also the conveying processing unit time may be determined to be an integer fraction of the preparation processing unit time. Further, the preparation processing unit time may be determined to be an integer multiple of the conveying processing unit time, and also the extraction processing unit time may be determined to be an integer multiple of the preparation processing unit time.

By determining the respective unit times in this manner, the processing timings for the respective steps for different test samples completely coincide (synchronize) with one another, and therefore, scheduling in which all the mechanisms of the genetic testing system can continue to perform processing without interruption so that the maximum processing performance is exhibited for all the test samples is obtained.

Incidentally, in the case where the number of the requested primary samples is large, by adopting a method in which the extraction processing unit time is used as a reference, and in the case where the number of the reaction samples is large, by adopting a method in which the conveying processing unit time is used as a reference, the maximum processing performance according to the requested test samples can be achieved. Further, in the case where the number of the nucleic acid samples is the largest, by determining the extraction processing unit time and the conveying processing unit time based on the preparation processing unit time for the nucleic acid samples, the maximum processing performance according to the requested test samples can be exhibited.

In FIG. 5-3, a method of determining the scheduling cycle according to each step determined based on the determination of the reference step is shown. Incidentally, also the process for determining the reference step is calculated by the control device or the calculating machine (not shown).

First, the control device determines the sample whose requested number is the largest, and determines the reference step (501). Subsequently, the control device controls the unit time for the other two steps according to the determined reference step (502 to 504). When the unit times of the respective steps are determined, the control device determines scheduling cycles according to the following rule (505).

M−1 times of the preparation unit processing step are assigned to one time of the extraction processing step.

N−1 times of the reading unit conveying processing step are assigned to one time of the preparation unit processing step.

One time which is the subtracted number of times for the preparation unit processing step is assigned to the processing of the sample from the extraction processing step.

One time for the reading unit conveying processing step is determined to be the processing of the sample from the extraction unit processing step or the processing of the sample from the preparation unit.

(1-4) Concentration Calculation Step Based on Quantitative Standard Sample

Finally, a step of calculating the concentrations of quantitative standard samples required for determining the concentration of the primary sample will be described. The genetic testing system (data processing unit 2033) according to this embodiment quantitatively determines the concentration values of the respective test samples (a primary sample, a nucleic acid sample, and a reaction sample) based on the measured fluorescence intensity. At this time, the genetic testing system according to this embodiment performs quantitative determination of an accurate concentration value independent on the difference in the loaded test sample and realizes minimization of the quantitative standard samples to be consumed by calculating a calibration curve according to each sample from the quantitative standard samples.

In FIGS. 6-1 and 6-2, concepts of a quantitative assay using the genetic testing system according to this embodiment are shown. FIG. 6-1 is a view imaginary showing that the genetic testing system according to this embodiment can perform quantitative calculation using one quantitative standard sample with respect to samples for which pretreatment methods are different although amplification targets are the same. In the case of this embodiment, in the memory unit/arithmetic unit 2035, a relationship between a concentration value in the case where each sample is loaded from a different step and an actually measured Ct value is stored for each of the four types of quantitative standard samples having different concentrations.

Specifically, a concentration value A of a quantitative standard sample in the case where it is loaded in the genetic testing system as a primary sample, a concentration value B of a quantitative standard sample in the case where it is loaded in the genetic testing system as a nucleic acid sample, a concentration value C of a quantitative standard sample in the case where it is loaded in the genetic testing system as a reaction sample, and an actually measured Ct value are stored. Hereinafter, a table storing the relationship is referred to as a standard DB. Among these values, the concentration values A, B, and C of the quantitative standard samples have been stored in the standard DB in advance. As the concentration values A, B, and C of the quantitative standard samples, values determined in advance when the testing reagents are provided are input.

In FIG. 6-2, a procedure for performing the measurement of the concentrations of the respective test samples including a step of creating the standard DB is shown. In the case of this embodiment, the analysis function is performed by the data processing unit 2033. Incidentally, with respect to one testing item, one series of quantitative standard samples is provided. Further, it is desirable that the concentration value of the quantitative standard sample is determined beforehand using the genetic testing system to be used for the testing. For example, the concentration value B of the quantitative standard sample for the nucleic acid sample is determined by using the genetic testing system after performing extraction from the quantitative standard sample using a nucleic acid extraction method recommended by the genetic testing system. Further, for example, the concentration value C of the quantitative standard sample for the reaction sample is determined by using the genetic testing system after performing preparation from the quantitative standard sample using a nucleic acid extraction method and a reaction sample preparation method recommended by the genetic testing system.

In the case where such a standard DB is present, prior to the measurement of the test sample, a operator performs the measurement of the quantitative standard samples having respective concentrations by the genetic testing system and calculates the Ct value of the quantitative standard samples (601). In the measurement at this time, it is not necessary to perform actual measurement for all the primary sample, the nucleic acid sample, and the reaction sample, but it is only necessary to perform a test from a given sample loading unit. By this measurement, the actually measured Ct value of the quantitative standard samples is determined and stored in the standard DB. Incidentally, the measurement operation and the operation of storing the actually measured Ct value in the standard DB are performed by, for example, the data processing unit 2033.

According to this, a state in which the measurement of a test sample can be performed is reached. For example, in the case where a operator determines that the primary sample is a testing target (in the case where the primary sample is loaded in the primary sample loading unit 205), the data processing unit 2033 creates a calibration curve for the primary sample by accessing the standard DB before starting the measurement of the primary sample (602 and 603). Specifically, the data processing unit 2033 reads the concentration values A1, A2, A3, and A4 of the quantitative standard samples for the primary sample with reference to the standard DB, and these values are plotted on the X-axis, and at the same time, the Ct values corresponding thereto are plotted on the Y-axis. Subsequently, the data processing unit 2033 draws two lines which pass through the corresponding plotted points and are parallel to the X-axis and the Y-axis, respectively, and an intersection point of these lines is plotted in the coordinate system. Thereafter, the data processing unit 2033 draws a line connecting these plotted points in the coordinate system, whereby a calibration curve for the primary sample is created.

Incidentally, as described above, the genetic testing system according to this embodiment can simultaneously perform the measurement of the respective types of the test samples. Therefore, in the case where the nucleic acid sample and the reaction sample are loaded from the corresponding sample loading units, the data processing unit 2033 also creates calibration curves corresponding to these samples.

When the creation of the calibration curve is completed, the data processing unit 2033 determines the Ct value of the reaction sample obtained for each test sample (604 and 605). Thereafter, the data processing unit 2033 fits the determined Ct value to the standard DB, and the concentration value of the primary sample having an unknown concentration is determined (606).

In this manner, the genetic testing system according to this embodiment can determine the concentrations of different type of samples (a primary sample, a nucleic acid sample, and a reaction sample) for one testing item by performing the measurement of one quantitative standard sample once in advance.

(Conclusion)

As described above, according to the genetic testing system of this embodiment, even if the type or property of the primary sample is different, testing can be performed by one genetic testing system. Therefore, there is no effect of the difference in systems as conventional systems, and thus, the reliability of the testing results and the inter-testing consistency can be ensured. Further, according to the genetic testing system of this embodiment, the using amount of the quantitative standard sample can be minimized, and thus, the measurement cost can be decreased as compared with the conventional systems. Further, in the case of the genetic testing system according to this embodiment, testing of different types of samples can be performed simultaneously in a parallel manner. Moreover, at this time, the maximum processing performance can be realized by optimizing the measurement timing for the respective test samples.

Other Embodiments

The invention is not limited to the embodiments described above and includes various modifications. For example, in the above-described embodiments, a part of the embodiments is described in detail for explaining the invention in an easy-to-understand manner, and it is not necessary to include all the described configurations. Further, a part of a certain embodiment can be replaced by the configuration of another embodiment, and the configuration of a certain embodiment can be added to the configuration of another embodiment. Further, it is also possible to add, delete, or replace another configuration with respect to a part of the configuration of each embodiment.

Further, the above-described respective configurations, functions, processing units, processing methods, etc. may be partially or entirely realized as, for example, an integrated circuit, or other hardware. Further, the above-described respective configurations, functions, etc. may be realized by interpreting and executing a program which realizes the respective functions by a processor. That is, they may be realized as software. The information of a program, a table, a file, or the like for achieving the respective functions can be stored in a recording device such as a memory, a hard disk, or an SSD (Solid State Drive), or a recording medium such as an IC card, an SD card, or a DVD.

As for the control lines or information lines, the ones which are considered necessary for the description are shown, but all the control lines or information lines required for the product are not necessarily shown. In fact, it can be considered that almost all the configurations are mutually connected to one another.

REFERENCE SINGS LIST

200: genetic testing system, 201: extraction unit, 202: reagent/reaction solution preparation unit, 203: reading unit, 204: conveying mechanism, 205: primary sample loading unit, 206: nucleic acid sample loading unit, 207: reaction sample loading unit

The invention claimed is:

1. A genetic testing system, comprising:
an extraction unit which includes a primary sample loading unit which loads one or more primary samples into the extraction unit, and the extraction unit prepares one or more first nucleic acid samples from the primary samples;
an assay preparation unit which includes a nucleic acid sample loading unit which loads one or more second nucleic acid samples into the assay preparation unit, and the assay preparation unit prepares one or more first reaction samples from the one or more first nucleic acid samples and the second nucleic acid samples;
a reading unit which measures the first reaction samples;
a first conveying mechanism which moves the one or more first nucleic acid samples to the assay preparation unit and the one or more first reaction samples to the reading unit;
a plurality of second conveying mechanisms which are respectively provided in the extraction unit to convey the primary samples and the one of more first nucleic acid samples therein, in the assay preparation unit to convey the one or more first nucleic acid samples, the one or more second nucleic acid samples, and the one or more first reaction samples therein, and in the reading unit to convey the one or more first reaction samples therein; and
a controller programmed to:
control the extraction unit, the assay preparation unit, the reading unit, the first conveying mechanism, and the second conveying mechanisms; and
determine a processing schedule among the extraction unit, the assay preparation unit, and the reading unit, and set an extraction processing unit time for the extraction unit to an integer multiple of a preparation processing unit time for the assay preparation unit.

2. The genetic testing system according to claim 1, wherein the reading unit includes a reaction sample loading unit which loads one or more second reaction samples into the reading unit.

3. A genetic testing system, comprising:
an extraction unit which includes a primary sample loading unit which loads one or more primary samples into the extraction unit, and the extraction unit prepares one or more first nucleic acid samples from the primary samples;
an assay preparation unit which includes a nucleic acid sample loading unit which loads one or more second nucleic acid samples into the assay preparation unit, and the assay preparation unit prepares one or more first reaction samples from the one or more first nucleic acid samples and the second nucleic acid samples;
a reading unit which measures the first reaction samples;
a first conveying mechanism which moves the one or more first nucleic acid samples to the assay preparation unit and the one or more first reaction samples to the reading unit;
a plurality of second conveying mechanisms which are respectively provided in the extraction unit to convey the primary samples and the one or more first nucleic acid samples therein, in the assay preparation unit to convey the one or more first nucleic acid samples, the one or more second nucleic acid samples, and the one or more first reaction samples therein, and in the reading unit to convey the one or more first reaction samples therein; and
a controller programmed to:
control the extraction unit, the assay preparation unit, the reading unit, the first conveying mechanism, and the second conveying mechanisms; and
determine a processing schedule among the extraction unit, the assay preparation unit, and the reading unit, and then set a processing unit time for the assay preparation unit to an integer multiple of a conveying processing unit time for the first conveying mechanism.

4. The genetic testing system according to claim 2, wherein controller is further programmed to:
determine a processing schedule among the extraction unit, the assay preparation unit, and the reading unit, and
determine respective processing unit times for the extraction unit, the assay preparation unit, and the reading unit based on which of a number of the primary samples, a number of the second nucleic acid samples, and a number of the second reaction samples is larger.

5. The genetic testing system according to claim 2, wherein the controller is further programmed to:
store a concentration information database for a plurality of test items, the concentration information database including concentration information for the primary samples loaded into the extraction unit, concentration information for the second nucleic acid samples loaded into the assay preparation unit, and concentration information for the second reaction samples loaded into the reading unit,
select the concentration information to be referred to from the concentration information database according to whether one of the first and second reaction samples corresponds to one of the primary samples, the first nucleic acid samples, or the second nucleic acid samples, and calculates a concentration value of the one of the first and second reaction samples based on the selected concentration information, create a calibration curve based on the selected concentration information, and calculate a concentration value of the one of the first and second reaction samples based on the created calibration curve.

6. The genetic testing system according to claim 1, wherein at least one of the second conveying mechanisms has two or more conveying lanes.

7. A genetic testing system, comprising:
an extraction unit which includes a primary sample loading unit which loads one or more primary samples into the extraction unit, and the extraction unit prepares one or more first nucleic acid samples from the primary samples;
an assay preparation unit which prepares one or more first reaction samples from the first nucleic acid samples;
a reading unit which includes a reaction sample loading unit which loads one or more second reaction samples into the reading unit, and the reading unit measures the one or more first and second reaction samples;
a first conveyor which moves the first nucleic acid samples to the assay preparation unit and the first reaction samples to the reading unit;
a plurality of second conveying mechanisms which are respectively provided in the extraction unit to convey the primary samples and the first nucleic acid samples therein, in the assay preparation unit to convey the first nucleic acid samples and the one or more first reaction samples therein, and in the reading unit to convey the one or more first reaction samples and the second reaction samples therein; and
a controller programmed to:
control the extraction unit, the assay preparation unit, the reading unit, the first conveying mechanism, and the second conveying mechanisms; and
determine a processing schedule among the extraction unit, the assay preparation unit, and the reading unit, and set an extraction processing unit time for the extraction unit to an integer multiple of a preparation processing unit time for the assay preparation unit.

8. The genetic testing system according to claim 7, wherein the controller is further programmed to:
determine a processing schedule among the extraction unit, the assay preparation unit, and the reading unit, and set a processing unit time for the assay preparation unit to an integer multiple of a conveying processing unit time for the first conveying mechanism.

9. The genetic testing system according to claim 7, wherein the controller is further programmed to:
determine a processing schedule among the extraction unit, the assay preparation unit, and the reading unit, and determine respective processing unit times for the extraction unit, the assay preparation unit, and the reading unit based on which of a number of the primary samples and a number of the second reaction samples is larger.

10. The genetic testing system according to claim 7, wherein the controller is further programmed to:
store a concentration information database for a plurality of test items, the concentration information database including concentration information for the primary samples loaded into the extraction unit, and concentration information for the second reaction samples loaded into the reading unit,
select the concentration information to be referred to from the concentration information database according to whether one of the first and second reaction samples corresponds to one of the primary samples or the second reaction samples, and calculates a concentration value of the one of the first and second reaction samples based on the selected concentration information, and
create a calibration curve based on the concentration information read from the concentration information database according to the one of the first and second reaction samples, and calculates a concentration value of the one of the first and second reaction samples based on the created calibration curve.

11. The genetic testing system according to claim 7, wherein at least one of the second conveying mechanisms has two or more conveying lanes.

* * * * *